United States Patent [19]

Martin et al.

[11] Patent Number: 5,614,545

[45] Date of Patent: *Mar. 25, 1997

[54] TOPICAL COMPOSITION FOR TREATMENT OF BLEPHARITIS

[75] Inventors: Neil F. Martin, Potomac; Howard N. Robinson, Lutherville, both of Md.

[73] Assignees: Leonard Bloom, Towson; Marvin S. Towsend, Rockville, both of Md.; a part interest

[*] Notice: The portion of the term of this patent subsequent to Sep. 18, 2010, has been disclaimed.

[21] Appl. No.: 477,089

[22] Filed: Jun. 7, 1995

Related U.S. Application Data

[63] Continuation of Ser. No. 969,194, Feb. 16, 1993, abandoned, which is a continuation-in-part of Ser. No. 568,461, Aug. 16, 1990, abandoned, which is a continuation-in-part of Ser. No. 204,547, Jun. 9, 1988, Pat. No. 4,957,918.

[51] Int. Cl.[6] ............... A61K 31/415; A61K 31/535
[52] U.S. Cl. .................... 514/398; 514/235.5
[58] Field of Search ................ 514/398, 235.5

[56] References Cited

U.S. PATENT DOCUMENTS 4,612,193  9/1986  Gordon et al. ................ 424/146

FOREIGN PATENT DOCUMENTS

| 2333500 | 7/1977 | France . |
| 2624736 | 6/1989 | France . |
| WO8906537 | 7/1989 | WIPO . |

OTHER PUBLICATIONS

Bleicher, et al., "Topical metronidazole therapy for rosacea," *Arch. Dermatol.* 123: 609–614 (1987).

Browning, et al., "Ocular Rosacea" *Survey of Ophthalmol.* 31: 145–158 (1986).

Mattila, et al., "Penetration of metronidazole and trindazole into the aqueous humor in man" *Chemotherapy* 29: 188–191 (1983).

*Primary Examiner*—Phyllis G. Spivack
*Attorney, Agent, or Firm*—Olson & Hierl, Ltd.

[57] ABSTRACT

A pharmaceutical composition for treating blepharitis or blepharoconjunctivitis is disclosed for topical administration comprising a nitroimidazole, as metronidazole, in a suitable ophthalmic carrier to be applied directly to affected ocular tissues. The carrier may be an artificial tear solution, an ointment, a water soluble gel, a nonaqueous carrier or an eyelash shampoo.

27 Claims, No Drawings

TOPICAL COMPOSITION FOR TREATMENT OF BLEPHARITIS

CROSS REFERENCE TO RELATED APPLICATIONS

This application is a continuation of application Ser. No. 07/969,194, filed Feb. 16, 1993, now abandoned, which is a continuation-in-part of application Ser. No. 07/568,461, filed Aug. 16, 1990, now abandoned which, in turn, is a continuation-in-part of application Ser. No. 07/204,547, filed Jun. 9, 1988 U.S. Pat. No. 4,957,918.

TECHNICAL FIELD

The present invention relates to the field of treating abnormal eye inflammation and more particularly to the topical treatment of inflammations and other dysfunctions of the eyelid and conjunctiva. The present invention is especially concerned with the treatment of meibomian gland dysfunction, blepharitis, and blepharoconjunctivitis particularly associated with ocular rosacea.

ART

Blepharitis is an inflammation of the eyelids. Blepharoconjunctivitis is an inflammation of the eyelids and the conjunctiva of the eye. Both conditions are associated with the condition known as ocular rosacea.

Rosacea is a disease of the skin (ache rosacea) and eyes (ocular rosacea) of unknown etiology and a variety of manifestations. The clinical and pathological features of the eye disease are nonspecific, and the disease is widely underdiagnosed by ophthalmologists.

More specifically with respect to ocular rosacea, ocular rosacea may involve the eyelids, conjunctiva, and cornea. Common manifestations of ocular rosacea include blepharitis, blepharoconjunctivitis, meibomianitis, chalazia, styes and conjunctival hyperemia.

References which discuss ocular rosacea include: "Ocular Rosacea" by M. S. Jenkins et al, American Journal of Ophthalmology, Vol. 88:618–622 (1979); "Blepharitis Associates With Ache Rosacea and Seborrheic Dermatitis" by J. P. McCulley et al, in Oculocutaneous Diseases, edited by J. P. Callen et al, Little, Brown & Company, International Ophthalmology Clinics, Spring 1985, Vol. 25, No. 1, pp. 159–172; and "Ocular Rosacea" by D. J. Browning et al, Survey of Ophthalmology, Vol. 31, No. 3, November-December 1986, pp. 145–158.

In the article by McCulley et al mentioned above, on pages 170–172, several treatments for blepharitis are disclosed. These treatments include: topical antibiotics; oral tetracycline; SSA neutralizers; exoenzymatic inhibitors; vitamin A analogs; and other means of affecting meibomian gland secretions.

In another prior art reference, Textbook of Dermatology, 4th Edition, A. Rook et al editors, Vol. 2, p. 3252, there is a disclosure that Demodectic blepharitis may be treated with bathing with boric acid or with benzalkonium chloride.

In the article by Browning et al mentioned above, on p. 155, there is a disclosure that for treatment of ocular rosacea only tetracycline has been critically studied. In the same article, there is mentioned that metronidazole has been used for treatment of skin lesions of rosacea. However, the article does not teach the use of a nitroimidazole compound (including metronidazole) with a suitable carrier for topical treatment of ocular tissues.

In another reference, namely "Topical Metronidazole Therapy for Rosacea", by P. A. Bleicher et al, Arch Dermatol., Vol. 123, May 1987, pp. 609–614, there is a disclosure that metronidazole can be used in a gel for treatment of rosacea of the skin. However, there is no disclosure that metronidazole can be used for ocular rosacea.

The prior art also teaches other treatments for eye inflammations using the direct application of a treating composition to the eye. For example, in U.S. Pat. No. 4,612,193 to Gordon et al, there is a disclosure that a blepharitic infection (not characterized as being caused by ocular rosacea) can cause a stye and that an ointment is provided to treat the stye. The ointment is based on yellow mercuric oxide, boric acid, and wheat germ oil.

In the book Diseases of the Cornea, 2nd Edition, by M. G. Grayson, C. Z. Mosby Company, 1983, pp. 119–209, there is a disclosure that blepharitis can be treated using antibiotic ointments containing antibiotics such as bacitracin, erythromycin, chloramphenicol, and tetracycline. Other active agents for treating blepharitis include Rifampin, a very dilute steroid such as 0.12%, prednisolone, and polysulfide.

The prior art treatments for eye inflammations have several disadvantages. For example, when tetracycline is taken orally it takes between two to three months to have a significant effect. Furthermore, tetracycline is plagued with side effects such as super infections, light sensitivity, cramp feelings of the user, contraindication if the user is pregnant, and resultant feelings that are similar to those when a person has the flu. Therefore, it would be desirable to avoid the use of tetracycline for the treatment of eye inflammations (e.g. ocular rosacea and related conditions).

Another eye condition is known as dry eye which results from an abnormal deficiency of tear production. A discussion of dry eye is found in the article entitled "Tear Physiology and Dry Eyes" by F. J. Holly et al, Survey of Ophthalmology, Vol. 22, No. 2, September-October 1977, pp. 69–87. As disclosed in the Holly et al article, the primary treatment for dry eye is the use of artificial tears applied topically. Unfortunately, blepharitis is often misdiagnosed as dry eye. As a result, treatment with artificial tears is inadequate to cure the patient's problem. It would be desirable to provide a pharmaceutical composition that would treat the actual blepharitis in the instance where the condition was misdiagnosed as dry eye.

Another problem that has received attention in the ophthalmological literature lately is infection by a parasite known as *Acanthamoeba hystolytica* which particularly plagues users of contact lenses. A particularly devastating infection results from this parasite leaving the victim particularly susceptible to blindness in an infected eye. A presently used treatment for Acanthamoeba is a therapeutic agent known as brolene which is an over-the-counter British stye medication. Other known treatments for Acanthamoeba include antibiotics such as micadasol and mediasforan. However, it would be desirable if another non-antibiotic agent could be applied topically to alleviate the deleterious conditions caused by the Acanthamoeba organism.

Another problem associated with wearers of contact lenses is the formation of film and deposits on the surface of the lenses. Lumpy deposits formed on the contact lenses are very often due to undiagnosed blepharitis. By alleviating the underlying blepharitis condition, the cause of deposit formation on contact lenses could be alleviated or removed. In this respect, it would be desirable to provide a treatment to prevent deposit formation on contact lenses that result from undiagnosed blepharitis.

The aforementioned contact lens surface film and deposits caused by blepharitis are associated with the formation of bumps (giant papillae) under the upper lids of contact lens wearers. This condition, giant papillary conjunctivitis (GPC), is an immune-mediated reaction to contact lens surface contamination and may require patients to discontinue contact lens wear. By alleviating the underlying blepharitis condition, the cause of the contamination which leads to GPC could be alleviated. This treatment may then allow certain wearers of contact lenses to resume use.

Still another option of the invention is to provide a treatment to prevent the development of the condition known as giant papillary conjunctivitis (GPC).

Although systemic treatments for eye conditions are known, such treatments are not popular with ophthalmologists. An eye doctor generally prefers to prescribe an eye medicine that is administered topically to the eye rather than prescribe a pill or the like which administers the medicine systemically. Therefore, it would be desirable to provide a treatment for blepharitis, or blepharoconjunctivitis, or ocular rosacea generally that is administered in a form such as a topically applied ointment or topically applied drops.

DISCLOSURE OF INVENTION

Accordingly, it is an object of the present invention to alleviate the disadvantages and deficiencies of the prior art by providing a treatment for meibomian gland dysfunction, blepharitis, blepharoconjunctivitis, and ocular rosacea that is administered in the form of eye drops or other topically administered eye preparations.

Another object of the invention is to provide a treatment that avoids the use of systemic tetracycline or other systemic antibiotics for treating ocular inflammations such as ocular rosacea and related conditions.

Another object of the invention is to provide a pharmaceutical composition that treats actual blepharitis in an instance where the actual condition is misdiagnosed as dry eye.

Still another object of the invention is to provide a topical treatment for the eye conditions resulting from infection by *Acanthamoeba hystolytica*.

Yet another object of the invention is to provide a treatment to prevent deposit formation on contact lenses that result from undiagnosed blepharitis and related giant papillary conjunctivitis (GPC).

In accordance with the teachings of the present invention, a pharmaceutical composition is provided for treating blepharitis and blepharoconjunctivitis generally and especially associated with ocular rosacea. The pharmaceutical composition of the invention includes an amount of nitroimidazole compound effective for treating the blepharitis and/or blepharoconjunctivitis and/or ocular rosacea; and a carrier for the nitroimidazole compound wherein the carrier is suitable for direct application to the eye tissues. The nitroimidazole compound is selected from the group consisting of metronidazole, nimorazole, tinidazole, ordinidazole, secnidazole, and carnidazole. The preferred compound is metronidazole.

The carrier may be in the form of an ointment, e.g. petrolatum-based or a water soluble gel, or in the form of a liquid to be applied to the eye in the form of eye drops. The eye drops can be in a bottle containing a plurality of doses or can be in a unidose dispenser.

One carrier for eye drops is an artificial tear composition including primarily isotonic sodium chloride. Other artificial tear ophthalmic carriers for the eye drops can be a hypertonic composition or a hypotonic composition based on sodium chloride solution. Moreover, other hypertonic, isotonic, and hypotonic carriers can be used. In addition, a cellulose ether such as methylcellulose may be added to the artificial tear carrier. Other cellulose ethers such as hydroxypropylmethylcellulose and hydroxyethylcellulose may be included in the artificial tear carrier. The artificial tear composition may also include a polyvinyl alcohol.

Another carrier administered in the form of eye drops can have a nonaqueous liquid base, e.g. a mineral oil based carrier. For example, the liquid ocular lubricant LIPO-TEARS, which contains a blend of mineral oil and white petrolatum U.S.P., can be used. The carrier LIPO-TEARS is made by Spectra Pharmaceutical Services, Inc., Hanover, Mass. 02339.

Yet another carrier for ocular administration of the nitroimidazole compound is a suspension of solid particles in a liquid. More specifically, the ocular administration can be in the form of an aqueous suspension. Even more specifically, a carrier for administering the nitroimidazole in suspension form can be particles of an ion-exchange resin, e.g. Amberlite, suspended in water. Employment of the ion-exchange resin Amberlite in an aqueous suspension for ocular administration of a betaxolol HCl treating agent (a beta-adrenergic blocker) for treating glaucoma is embodied in BETOPIC®S made by Alcon Laboratories, Inc., Fort Worth, Tex. 76134.

The composition of the invention is applied to ocular tissues directly for treating the conditions of blepharitis, blepharoconjunctivitis, and ocular rosacea.

Another carrier for the nitroimidazole compound can be a shampoo formulation. In this respect, the nitroimidazole compound can be part of an eyelash shampoo or eyescrub for cleansing hair associated with the eye. Other carriers for the metronidazole compounds can be slow release inserts, aerosols, collagen shields, bandage contact lenses, and contact lens solutions.

In yet another aspect of the invention, the nitroimidazole compound can be used in conjunction with a shampoo formulation intended to be used on the scalp areas. This formulation can be used for treating rosacea of the scalp or for hair or fur infestations of *Demodex follicularum* (mange).

These and other objects and advantages of the present invention will become apparent from a reading of the following specification.

MODE FOR CARRYING OUT THE INVENTION

Here are represented several formulations for pharmaceutical compositions of the invention.

EXAMPLE 1

One gram of metronidazole is added to 1,000 grams of artificial tear carrier with stirring. The artificial tear carrier is isotonic sodium chloride solution. This formulation provides an approximately 0.1% solution of metronidazole in artificial tear carrier for application to the patent by means of eye drops.

EXAMPLE 2

One gram of metronidazole is added to 1,000 grams of artificial tear carrier with stirring. The artificial tear carrier is hypertonic sodium chloride solution. This formulation provides an approximately 0.1% solution of metronidazole in artificial tear carrier for application to the patent by means of eye drops.

EXAMPLE 3

One gram of metronidazole is added to 1,000 grams of artificial tear carrier with stirring. The artificial tear carrier is hypotonic sodium chloride solution. This formulation provides an approximately 0.1% solution of metronidazole in artificial tear carrier for application to the patent by means of eye drops.

EXAMPLE 4

7.5 grams of metronidazole are added to 992.5 grams of artificial tear solution with stirring to provide a formulation containing approximately 0.75% metronidazole in an artificial tear carrier.

EXAMPLE 5

10 grams of metronidazole are added to 990.0 grams of isotonic sodium chloride solution with stirring to provide a 1% metronidazole solution in isotonic sodium chloride carrier.

EXAMPLE 6

An eye drop formulation is made up by blending the following: 10 grams metronidazole, 10 grams methylcellulose, and 980 grams isotonic sodium chloride. This formulation contains approximately 1% metronidazole, 1% methylcellulose, and the balance being isotonic sodium chloride carrier.

EXAMPLE 7

Another eye drop formulation is made up by blending the following: 10 grams, 14 grams polyvinyl alcohol, and 976 grams isotonic sodium chloride artificial tear solution. The resulting formulation contains approximately 1% metronidazole, 1.4% polyvinyl alcohol, and the balance being artificial tear carrier.

EXAMPLE 8

Another eye drop formulation is made by blending the following: 15 grams metronidazole and 985 grams of isotonic sodium chloride artificial tear solution with stirring to provide a 1.5% metronidazole solution.

EXAMPLE 9

Another eye drop formulation is made by stirring 20 grams metronidazole into 980 grams of artificial tear solution to provide a 2.0% metronidazole solution.

In addition to the artificial tear carriers disclosed above, an artificial tear carrier for the nitroimidazole compound can be selected from an artificial tear formulation selected from the formulations set out in Table I below.

TABLE I

| Major Component | Trade Name | Preservative |
| --- | --- | --- |
| Hydroxyethyl-cellulose | Clerz | thimerosal + edetate disodium |
|  | Lyteers | benzalkonium chloride + edetate |

TABLE I-continued

| Major Component | Trade Name | Preservative |
| --- | --- | --- |
|  | Teargard | disodium thimersal + ededate disodium |
| Hydroxypropyl-cellulose | Lacrisert* (Water soluble insert) | benzalkonium chloride + edetate disodium |
| Hydroxpropl methycellulbse | Isopto Alkaline | benzalkonium chloride |
|  | Isopto Plain | benzalkonium chloride |
|  | Isopto Tears | benzalkonium chloride |
|  | Lacril | chlorobutanol |
|  | Muro Tears | benzalkonium chloride + edetate disodium |
|  | Tearisol | benzalkonium chloride + edetate disodium |
| Methylcellulose | Methopto | benzalkonium chloride |
|  | Methulose | benzalkonium chloride |
|  | Murocel | methylparaben & propylparaben |
| Carboxymethyl-cellulose | Celluvisc | preservative free |
|  | Visculose | benzalkonium chloride |
| Polyvinyl alcohol | Aqua Tears | benzalkonium chloride + edetate sodium |
|  | Liquifilm Tears | chlorobutanol |
|  | Liquifilm Forte | thimerosal + edetate sodium |
|  | Tears Plus | chlorobutanol |
| Polyvinyl alcohol and cellulose ester | aqua-FLOW | benzalkonium chloride + edetate disodium |
|  | Neo-Tears | thimerosal + edetate disodium |
| Polyvinyl alcohol and povidone | Refresh | preservative free |
| Other Polymeric Systems | Adapettes | thimerosal & edetate disodium |
|  | Adsorbotear | thimerosal & edetate disodium |
|  | Comfort Drops | benzalkonium chloride + edetate disodium |
|  | Dual Wet | benzalkonium chloride + edetate disodium |
|  | Hypotears | benzalkonium chloride + edetate disodium |
|  | Tears Naturale | benzalkonium chloride + edetate disodium |

More complete descriptions of artificial tear carriers are found in PDR for Nonprescription Drugs, 1990, pages 504–506.

Moreover, the TEARS NATURAL® is made by Alcon, (6201 South Freeway, Fort Worth, Tex. 76134) and is comprised of DUASORB® (Dextran 70 Hydroxypropyl Methylcellulose) as a water soluble polymeric system with preservatives benzalkonium chloride, 0.01% and Edetate Disodium 0.05% which is disclosed in U.S. Pat. No. 4,039,662, incorporated herein by reference.

EXAMPLE 10

The following ointment can be prepared by blending 10 grams of metronidazole thoroughly with 990 grams petrolatum vehicle (an ointment base) to provide an ointment suitable for application to the ocular tissues which contains 1% metronidazole.

EXAMPLE 11

The following ointment can be prepared by blending 15 grams of metronidazole thoroughly with 985 grams petrolatum vehicle (an ointment base) to provide an ointment suitable for application to the ocular tissues which contains 1.5% metronidazole.

EXAMPLE 12

The following ointment can be prepared by blending 15 grams of metronidazole thoroughly with 980 grams petrolatum vehicle (an ointment base) to provide an ointment suitable for application to the ocular tissues which contains 2% metronidazole.

Other ointments based upon the petrolatum carrier can be selected from the carriers listed below in Table II.

TABLE II

| Trade Name | Composition |
| --- | --- |
| Akwa-Tears (Akorn) | Petrolatum, Liquid Lanolin, Mineral Oil |
| Duolube (Muro) | Sterile ointment containing white petroleum and mineral oil |
| Duratears (Alcon) | Sterile ointment with white petroleum, liquid lanolin, mineral oil, methylparaben and polyparaben |
| Hypotears (Cooper Vision) | Sterile ointment containing white petroleum and light mineral oil |
| Lacri-Lube S.O.P. (Allergan) | Sterile ointment with 42.5% mineral oil, 55% white petrolatum, lanolin, and chlorobutanol |

An ophthalmic gel carrier can also be used for administering the nitroimidazole compound directly to ocular tissues. A suitable ophthalmic gel carrier is comprised of approximately 10% CARBOPOL 940 (which is a synthetic high molecular weight cross-linked polymer of acrylic acid to impart a high viscosity. A specific formulation of the invention which employs an ophthalmic gel is set forth below in Example 13.

EXAMPLE 13

An aqueous gel formulation of the invention is obtained by blending approximately 20 grams of metronidazole with approximately 980 grams of an ophthalmic gel carrier containing approximately 0.08 grams of benzalkonium chloride, 0.5 grams of Edetate Disodium, 80 grams of Carbopol 940, and approximately 900 grams of water.

Another ophthalmic gel carrier can be prepared in accordance with the teaching in U.S. Pat. No. 4,788,007 incorporated herein by reference. This patent discloses an aqueous aloe vera gel. To obtain a composition for treating blepharitis in accordance with the subject invention, a quantity of metronidazole is added to a quantity of the aloe vera gel. More specifically, to obtain a gel formulation containing approximately 2% metronidazole, approximately 20 grams of metronidazole are blended with approximately 980 grams of the aloe vera gel.

As stated above, a shampoo which carries a nitroimidazole compound can be used for cleansing eyelashes and for treating ocular rosacea, blepharitis, and blepharoconjunctivitis. In Example 14 below, a formulation for an eyelash shampoo which carries the nitroimidazole compound, metronidazole, is presented.

EXAMPLE 14

The following eyelash shampoo can be prepared by adding 20 grams of metronidazole to approximately 1,000 grams of an eyelid cleanser known as I-SCRUB™ made by Spectra Pharmaceutical Services, Hanover, Mass., that contains the following ingredients: PEG-200 Glyceryl Monotallowate, Disodium Laureth Sulfosuccinate, Cocoamido Propyl Amine Oxide, PEG-78 Glyceryl Monococate, Benzyl Alcohol, Disodium Edetate, and Purified Water USP. I-SCRUB™ (without the presence of the subject metronidazole) is disclosed as being suitable for hygienic care of blepharitis. With the added metronidazole, the eyelash shampoo of the invention is effective in treating the blepharitis.

By employing the principles of the invention, numerous objects are realized and numerous benefits are obtained. For example, a pharmaceutical composition is provided to treat blepharitis, blepharoconjunctivitis, and ocular rosacea and is administered in the form of an ointment or in the form of eye drops. The method of treatment of the invention avoids the use of tetracycline for treating ocular rosacea and related conditions. With the invention, a pharmaceutical composition is provided that treats actual blepharitis in the case where the condition is misdiagnosed as dry eye. The invention provides a topical treatment for eye conditions resulting from infection by *Acanthamoeba hystolytica*. The invention provides a treatment to prevent deposit formation on contact lenses that results from blepharitis and related giant papillary conjunctivitis.

Obviously, many modifications may be made without departing from the basic spirit of the present invention. Accordingly, it will be appreciated by those skilled in the art that within the scope of the appended claims, the invention may be practiced other than has been specifically described herein.

We claim:

1. An ophthalmic pharmaceutical composition suitable for direct instillation into the eye and comprising:

a nitroimidazole compound present in an amount in the range of 0.1–2% by weight of the composition and effective to treat blepharitis and blepharoconjunctivitis in an animal or human patient; and an ophthalmic carrier for said nitroimidazole compound, said carrier being suitable for topical application to ocular tissues.

2. The pharmaceutical composition described in claim 1 wherein said carrier includes an ointment base suitable for direct application to the eye.

3. The pharmaceutical composition described in claim 2 wherein said ointment includes a petrolatum-based vehicle.

4. The pharmaceutical composition described in claim 1 wherein said carrier includes a water soluble gel.

5. The pharmaceutical composition described in claim 1 wherein said carrier includes a liquid suitable for application to the eye in the form of drops.

6. The pharmaceutical composition described in claim 1 wherein said nitroimidazole compound is present in a range of 0.75–1% and the balance being said carrier.

7. The pharmaceutical composition described in claim 1 wherein said nitroimidazole compound is present in a range of 0.75–2% and the balance being said carrier.

8. The pharmaceutical composition described in claim 1 wherein said nitroimidazole compound is selected from the group consisting of metronidazole, nimoranzole, tinidazole, ordinidazole, secnidazole, and carnidazole.

9. The composition described in claim 1 wherein said nitroimidazole compound is metronidazole.

10. The pharmaceutical composition described in claim 1 wherein said carrier includes a nonaqueous liquid base.

11. The pharmaceutical composition described in claim 1 wherein said carrier includes a mineral oil base.

12. The pharmaceutical composition described in claim 1 wherein said carrier includes a blend of mineral oil and petrolatum.

13. The pharmaceutical composition described in claim 1 wherein said carrier includes a suspension of solid particles in a liquid.

14. The pharmaceutical composition described in claim 1 wherein said carrier includes a suspension of an ion-exchange resin in water.

15. The pharmaceutical composition described in claim 14 wherein said ion-exchange resin includes Amberlite.

16. A pharmaceutical composition, comprising:

an amount of nitroimidazole compound effective to treat blepharitis and blepharoconjunctivitis in an animal or human patient; and a carrier for said nitroimidazole compound, said carrier suitable for topical application to ocular tissues, wherein said carrier includes an artificial tear composition which is either hypertonic, isotonic, or hypotonic.

17. The pharmaceutical composition described in claim 16 wherein said artificial tear composition includes a cellulose ether.

18. The pharmaceutical composition described in claim 17 wherein said cellulose ether is present as approximately 1% by weight of said artificial tear carrier.

19. The pharmaceutical composition described in claim 17 wherein said cellulose is selected from the group consisting of methylcellulose, hydroxypropylmethylcellulose, and hydroxyethylcellulose.

20. The pharmaceutical composition described in claim 19 wherein said cellulose ether is methylcellulose.

21. The pharmaceutical composition described in claim 16 wherein said artificial tear composition includes polyvinyl alcohol.

22. The pharmaceutical composition described in claim 21 wherein said polyvinyl alcohol is present as approximately 1.4% by weight of said artificial tear carrier.

23. A pharmaceutical composition, comprising:

an amount of nitroimidazole compound effective to treat blepharitis and blepharoconjunctivitis in an animal or human patient; and a hypotonic carrier for said nitroimidazole compound, said carrier suitable for topical application to ocular tissues.

24. A pharmaceutical composition, comprising:

an amount of nitroimidazole compound effective to treat blepharitis and blepharoconjunctivitis in an animal or human patient; and a hypertonic carrier for said nitroimidazole compound, said carrier suitable for topical application to ocular tissues.

25. A pharmaceutical composition, comprising:

an amount of nitroimidazole compound effective to treat blepharitis and blepharoconjunctivitis in an animal or human patient; and an isotonic carrier for said nitroimidazole compound, said carrier suitable for topical application to ocular tissues.

26. A pharmaceutical composition, comprising:

an amount of a nitroimidazole compound effective to treat blepharitis and blepharoconjunctivitis in an animal or human patient; and a carrier for said nitroimidazole compound, said carrier suitable for topical application to ocular tissues, wherein said carrier is a shampoo suitable for cleansing eyelashes.

27. A pharmaceutical composition, comprising:

an amount of a nitroimidazole compound effective to treat rosacea of the scalp in an animal or human patient; and a carrier for said nitroimidazole compound, said carrier suitable for topical application to scalp tissues, wherein said carrier is a shampoo suitable for cleansing the scalp and hair or fur.

* * * * *